United States Patent [19]

Taniguchi

[11] Patent Number: 5,658,774
[45] Date of Patent: Aug. 19, 1997

[54] IRF-1 DNA EXPRESSION INHIBITS GROWTH OF CELLS EXPRESSING C-MYC OR FOSB

[75] Inventor: Tadatsugu Taniguchi, Ibaraki, Japan

[73] Assignee: Boehringer Ingelheim International GmbH, Germany

[21] Appl. No.: 325,944

[22] Filed: Oct. 19, 1994

[30] Foreign Application Priority Data

Oct. 19, 1993 [EP] European Pat. Off. .............. 93116854

[51] Int. Cl.$^6$ .................................................... C12N 15/00
[52] U.S. Cl. ...................................... 435/172.3; 435/320.1
[58] Field of Search ............................. 435/172.3, 320.1; 514/44; 424/93.21

[56] References Cited

FOREIGN PATENT DOCUMENTS

| | | |
|---|---|---|
| 0 355 190 | 2/1990 | European Pat. Off. . |
| 0 359 998 | 3/1990 | European Pat. Off. . |
| 0 535 576 | 4/1993 | European Pat. Off. . |
| WO93/07283 | 4/1993 | WIPO . |
| WO94/06818 | 3/1994 | WIPO . |

OTHER PUBLICATIONS

Tanaka et al., "Recognition DNA Sequences of Interferon Regulatory Factor 1 (IRF-1) and IRF-2, Regulators of Cell Growth and the Interferon System," *Mol. Cell. Biol.* 13 (8):4531–4538 (1993).

Tanaka, N., et al., "Cellular Commitment to Oncogene–Induced Transformation or Apoptosis is Dependent on the Transcription Factor IRF-1," *Cell* 77:829–839 (Jun. 17, 1994).

Cotten et al., "High–efficiency receptor–mediated delivery of small and large (48 kilobase gene constructs using the endosome–disruption activity of defective or chemically inactivated adenovirus particles," *PNAS* 89:6094–6098 (Jul. 1992).

Curiel et al., "Andenovirus enhancement of transferrin–polylysine–mediated gene delivery," *PNAS* 88:8850–8854 (Oct. 1991).

Curiel et al., "Gene Transfer to Respiratory Epithelial Cells via the Receptor–mediated Endocytosis Pathway," *Am. J. Respir. Cell Mol. Biol.* 6:247–252 (1992).

Curiel et al., "High–Efficiency Gene Transfer Mediated by Adenovirus Coupled to DNA–Polylysine Complexes," *Human Gene Therapy* 3:147–154 (1992).

Dhawan et al., "Systemic Delivery of Human Growth Hormone by Injection of Genetically Engineered Myoblasts," *Science* 254:1509–1512 (Dec. 6, 1991).

Eaton et al., "Construction and Characterization of an Active Factor VIII Variant Lacking the Central One–Third of the Molecule," *Biochem.* 25:8343–8347 (Dec. 30, 1986).

Harada et al., "Anti–Oncogenic and Oncogenic Potentials of Interferon Regulatory Factors–1 and –2," *Science* 259:971–974 (Feb. 12, 1993).

Luthman & Magnusson, "High efficiency polyoma DNA transfection of chloroquine treated cells," *Nucl. Acids Res.* 11:1295–1308 (1983).

Maruyama et al., "Sequence of cDNA coding for human IRF–1," *Nucl. Acids Res.* 17:3292 (1989).

Miyamoto et al., "Regulated Expression of a Gene Encoding a Nuclear Factor, IRF–1, That Specifically Binds to IFN–β Gene Regulatory Elements," *Cell* 54:903–913 (Sep. 9, 1988).

Morgan & Anderson, "Human Gene Therapy," *Annu. Rev. Biochem.* 62:191–217 (1993).

Nakabeppu et al., "Proliferative Activiation of Quienscent Rat–1A Cells by ΔFosB," *Mol. Cell. Biol.* 13:4157–4166 (Jul. 1993).

Ponder et al., "Mouse hepatocytes migrate to liver parenchyma and function indefinitely after intrasplenic transplantation," *PNAS* 88:1217–1221 (Feb. 1991).

Roemer & Friedmann, "Concepts and strategies for human gene therapy," *Eur. J. Biochem.* 208:211–225 (1992).

Shiroki et al., "Neoplastic Transformation of Rat 3Y1 Cells by a Transcriptionally Activated Human c–myc Gene and Stabilization of p53 Cellular Tumor Antigen in the Trandformed Cells," *Mol. Cell. Biol.* 6:4379–4386 (Dec. 1986).

Wagner et al., "Coupling of adenovirus to transferrin–polylysine/DNA complexes greatly enhances receptor–mediated gene delivery and expression of transfected genes" *PNAS* 89:6099–6103 (Jul. 1992).

Wagner et al., "DNA–Binding Transferrin Conjugates as Functional Gene–Delivery Agents: Synthesis by Linkage of Polylysine or Ethidium Homodimer to the Transferrin Carbonydrate Moiety," *Bioconjugate Chem.* 2:226–231 (1991).

Wagner et al., "Transferrin–polycation–DNA complexes: The effect of polycations on the structure of the complex and DNA delivery to cells," *PNAS* 88:4255–4259 (May 1991).

Willman et al., "Deletion of IRF–1, Mapping to Chromosome 5q31.1, in Human Leukemia and Preleukemic Myelodysplasia," *Science* 259:968–971 (Feb. 12, 1993).

Zatloukal et al., "Transferrinfection: A Highly Efficient Way to Express Gene Constructs in Eukaryotic Cells," *Ann. New York Acad. Sci.* 660:136–153 (1992).

*Primary Examiner*—Deborah Crouch
*Attorney, Agent, or Firm*—Sterne, Kessler, Goldstein & Fox P.L.L.C.

[57] ABSTRACT

The present invention relates to a method of altering the phenotype of cells expressing an oncogene by expressing a nucleic acid encoding interferon regulatory factor 1 (IRF-1).

5 Claims, 2 Drawing Sheets

IRF-1 DNA EXPRESSION INHIBITS GROWTH OF CELLS EXPRESSING C-MYC OR FOSB

BACKGROUND OF THE INVENTION

1. Field of the Invention

The present invention relates to a method of altering the phenotype of cells expressing an oncogene by expressing a nucleic acid encoding interferon regulatory factor 1 (IRF-1).

2. Background Information

Interferon regulatory factor-1 (IRF-1), a transcriptional activator, and IRF-2, its antagonistic repressor, have been identified as regulators of type I interferon (IFN) and IFN-inducible genes. It has been shown previously that IRF-1 manifests anti-oncogenic activity in NIH 3T3 cells which are transformed with IRF-2, a natural antagonist of IRF-1. When the IRF2 gene was overexpressed in NIH 3T3 cells, the cells displayed enhanced tumorigenicity in nude mice. However, this phenotype was reversed by concomitant overexpression of the IRF-1 gene (Harada et al., Science 259: 971–974 (1993)). It has been shown that the human IRF-1 gene maps to chromosome 5q31.1, a region frequently deleted in patients with leukemia or preleukemic myelodysplastic syndromes (Willman et al., Science 259: 968–971 (1993)).

SUMMARY OF THE INVENTION

In the present invention, it has been found that interferon regulatory factor-1 (IRF-1) not only reverses the phenotype associated with cells transformed by IRF-2 (the natural antagonist of IRF-1), but also the phenotype (more specifically, the tumorigenic phenotype) of cells expressing oncogenes. Thus, in general, the invention provides a method of suppressing the tumorigenicity of cells expressing an oncogene. More specifically, the invention provides a method of suppressing the tumorigenicity of cells expressing an oncogene by expressing a nucleic acid encoding interferon regulatory factor 1 (IRF-1) such that the tumorigenicity is suppressed.

Further objects and advantages of the present invention will be clear from the description that follows.

DETAILED DESCRIPTION OF THE INVENTION

Figure 1A:
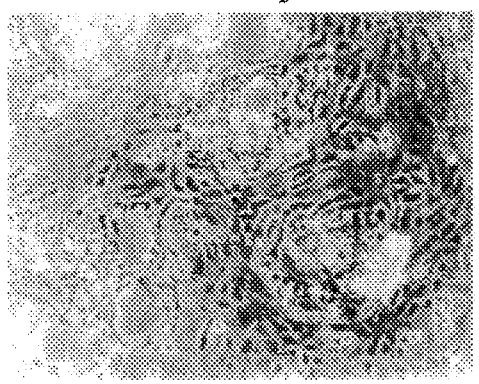
FIG. 1(A–F): Photographs of phenotypically reverted c-myc-transformed 3Y1 cells following retroviral introduction of IRF-1. The cells were all photographed (magnification, ×100) in Dulbecco modified Eagle medium containing 10% fetal calf serum. 3Y1-c-myc (FIG. 1A); c-myc-transformed 3Y1 cells (RmycY1), 3Y1 (FIG. 1B); untransformed rat 3Y1 cells, myc-IRF1-1 (FIG. 1C) and myc-IRF1-2 (FIG. 1E); pGDIGF1 infected RmycY1 cell clones, myc-C-1 (FIG. 1D) and myc-C-2 (FIG. 1F); control virus pGD (Harada et al., Science 259: 971–974 (1993) infected RmycY1 cell clones.

The present invention relates to altering the phenotype of cells by expressing a nucleic acid encoding interferon regulatory factor 1 (IRF-1). In one preferred embodiment, the invention relates to a method of suppressing the tumorigenicity of cells expressing an oncogene comprising expressing a nucleic acid encoding IRF-1 such that the tumorigenicity is suppressed. Interferon regulatory factor 1 (IRF-1) is defined herein to include biologically active variants or fragments thereof. Oncogenes as defined herein do not include IRF-2 since IRF-2 is the natural antagonist of IRF-1. In one preferred embodiment, the oncogene is c-myc or fosB. In a further preferred embodiment, the suppression of tumorigenicity is indicated by the reversal of the phenotype of the oncogenic cells. It is further preferred that the cells are characterized by lack or shortage of tumor suppressor gene expression.

A preferred embodiment of the present invention is directed to the gene transfer of a nucleic acid encoding interferon regulatory factor 1 (IRF-1) or a biologically active variant or fragment thereof into transformed or cancer cells. Advantageously, the nucleic acid is incorporated into an expression vector. This can be, for example, a viral vector, preferably a retroviral vector, e.g. pDG. In another preferred embodiment, the nucleic acid molecule is complexed with a conjugate, the conjugate consisting of an endosomolytical agent and a DNA binding agent (see below). Preferably, the endosomolytical agent is an inactivated adenovirus and the DNA-binding agent is polylysine.

The present invention is further related to the use of a nucleic acid containing the coding information for IRF-1 or a biologically active variant fragment thereof for the manufacture of a pharmaceutical composition for the therapy of cancer, especially when the pharmaceutical composition is suited for the gene therapy cancer.

In a further aspect, the present invention is related to a pharmaceutical composition for the therapy of cancer, characterized in that it contains a nucleic acid containing the coding information for IRF-1 or a biologically active variant or fragment thereof. The nucleic acid may also contain regulatory sequences.

In another aspect, the present invention is related to the use of IRF-1 polypeptide or a biologically active variant or fragment thereof for the manufacture of a pharmaceutical composition for the therapy of cancer and to a pharmaceutical composition containing IRF-1 polypeptide or a biologically active variant or fragment thereof.

Furthermore, the present invention is related to a method to reverse the phenotype of oncogenic cells, characterized in that a nucleic acid is transferred into the cells, the nucleic acid containing the coding information for IRF-1 and capable of expressing IRF-1 or a biologically active variant or fragment thereof. The IRF-1 of the present invention comes preferably from the same species as the cells which are to be treated. If human cells are to be treated, the IRF-1 is preferably human IRF-1. One skilled in the art knows how to produce nucleic acid molecules containing the coding information for IRF-1, for example IRF-1 from mouse (Myamoto et al., Cell 54: 903–913 (1988)) or man (Maruyama et at., Nucl. Acids Res.7: 3292 (1989); EP 0359998).

One skilled in the art also knows how to generate nucleic acid molecules coding for variants or fragments and methods to test whether such variants or fragments still exhibit the biological activity of the parent molecule. Thus, such variants and fragments are also encompassed by the present invention. The skilled expert further knows methods from the art how to integrate the coding information for IRF-1 into nucleic acids capable of expressing the gene, and to introduce such nucleic acid molecules into cells in a way that the IRF-1 gene is expressed in the target cells. More detailed examples how the present invention can be carried out are described below.

The present invention reverts the oncogenic phenotype of rat Rat 1 cells transformed by either c-myc gene or fosB gene. These two genes are well known oncogenes and their properties have been well studied (Shiroki et al., *Mol. Cell. Biol.* 6: 4379–4386 (1986); Nakabeppu et al., *Mol. Cell. Biol.* 13: 4157–4166 (1993)). A retrovirus, pDGIRF1, which expresses murine IRF-1 upon infection, was previously constructed (Harada et al., *Science* 259: 971–974 (1993)). The c-myc-transformed 3Y1 cell or fosB-transformed Rat-1A cell, termed RmycY1 and Rat-IA(FosB), respectively, both show anchorage-independent growth and enhanced tumorigenicity in rat or nude mice (Shiroki et al., *Mol. Cell. Biol.* 6: 4379–4386 (1986); Nakabeppu et al., *Mol. Cell. Biol.* 13: 4157–4166 (1993)).

The results suggest that some of the cancer cells may have either a completely or partially suppressed phenotype. Hence, the present invention can be used for gene therapy of cancer, especially for cancers which contain activated oncogenes or are characterized by lack or shortage of tumor suppressor gene expression. It can be also emphasized that the IRF-1 gene transfer can be achieved not only by the presently employed retrovirus but also by other means, i.e. the present invention is not restricted to the use of the IRF-1-expressing retrovirus, rather, it points to the general importance of IRF-1 transfer in the suppression of minor cells. Reviews of gene transfer systems and clinical protocols which can be adapted for use of the present invention can be found in the literature (Morgan and Anderson, *Ann. Rev. Biochem.* 62: 191–217 (1993); Roemer and Friedmann, *Eur. J. Biochem.* 208: 211–225 (1992)).

A gene transfer system which can be used advantageously in connection with the present invention has been developed recently (Curiel et al., *Proc. Natl. Acad. Sci. USA* 88: 8850–8854 (1991); Curiel et al., *Am. J. Respir. Cell Mol. Biol.* 6: 247–252 (1992a ); Zatloukal et al., *Ann. New York Acad Sci.* 660: 136–153 (1992); Cotten et al., *Proc. Natl. Acad. Sci. USA* 89: 6094–6098 (1992); Wagner et al., *Proc. Natl. Acad. Sci. USA* 89: 6099–6103 (1992); Curiel et al., *Human Gene Therapy* 3: 147–154 (1992b); Curiel et al. U.S. Ser. No. 07/948,357; Curiel et al. U.S. Ser. No. 08/166,899). It is based on the property of viruses, e.g. attenuated adenoviruses, to discharge the content of endosomes after having been incorporated by receptor-mediated endocytosis. The use of adenoviruses enhances the efficiency of gene transfer because it circumvents the lysosomal degradation of internalized DNA. The adenovirus can be modified by conjunction with polylysine. Since polylysine is cationic under physiological conditions, the resulting conjugate can complex DNA, for example DNA coding for IRF-1, by electrostatic interactions. The adenovirus-polylysine conjugates can be used to complex DNA together with transferrin-polylysine conjugates, resulting in ternary adenovirus-polylysine/transferrin-polylysine/DNA complexes (Wagner et al., loc. cit (1992)). Such complexes can bind to receptors specific for adenoviruses and/or transferrin and are internalized afterwards. After endocytosis, the adenovirus causes the break of the endosomal membrane and its content is discharged into the cytoplasm. The IRF-1-coding DNA can enter the cell nucleus, where IRF-1 is expressed mainly by episomally localized DNA.

In another embodiment, the present invention relates to a method of administering the IRF-1 gene to an animal (preferably, mammals, birds, fish, and reptiles (specifically, dogs, cats, rabbits, horses and humans; most preferably, humans)) in an amount sufficient to reduce tumorigenicity in said animal. The administered IRF-1 gene could specifically affect oncogene associated functions.

One skilled in the art will appreciate that the amounts to be administered for any particular treatment protocol can readily be determined. The dosage should not be so large as to cause adverse side effects, such as unwanted cross-reactions, anaphylactic reactions, and the like. Generally, the dosage will vary with the age, condition, sex and extent of disease in the patient, counter indications, if any, and other such variables, to be adjusted by the individual physician.

In another embodiment, the present invention relates to conjugate technology. The optimum transfer of nucleic acid into the cell can be achieved if the ratio of conjugate to nucleic acid is selected so that the internalizing factor-polycation/nucleic acid complexes are substantially electroneutral. The quantity of nucleic acid taken up into the cell is not reduced if some of the transferrin-polycation conjugate is replaced by non-covalently bound polycation; in certain cases there may even be a substantial increase in DNA uptake (Wagner, E. et al. (1991) *Proc. Natl. Acad. Sci. USA* 88, 4255–4259). It had been observed that the DNA of the complexes is present in a form compressed into toroidal structures with a diameter of 80 to 100 nm. The quantity of polycation is thus selected, with respect to the two parameters of electroneutrality and the achievement of a compact structure, while the quantity of polycation which results from the charging of the nucleic acid, with respect to achieving electroneutrality, generally also guarantees compacting of the DNA.

Thus, in a further embodiment of the invention, the complexes also contain nucleic acid-binding substances in a non-covalently bound form, which may be identical to or different from the binding factor. In case the endosomolytic agent is free virus, the complexes comprise nucleic acid and internalizing factor conjugate. In the case of an endosomolytic, e.g. a viral conjugate is employed, the nucleic acid is complexed with this conjugate, optionally in concert with a conjugate of an additional internalizing factor. The choice of non-covalently bound "free" substances having an affinity for nucleic acid, in their nature and quantity, is also determined by the conjugate(s), particularly taking account of the binding factor contained in the conjugate: if, for example, the binding factor is a substance which has no or limited capacity for DNA condensation, it is generally advisable, with a view to achieving efficient internalization of the complexes, to use substances having an affinity for DNA which possess this property in a high degree. If the binding factor itself is a nucleic acid condensing substance and if it has already brought about compacting of the nucleic acid sufficient for effective internalization, it is advisable to use a substance having an affinity for nucleic acid which brings about an increase in expression by virtue of other mechanisms.

The suitable "free" substances having an affinity for nucleic acid according to the invention include compounds capable of condensing nucleic acid and/or of protecting them from undesirable degradation in the cells, particularly the substances of a polycationic nature mentioned hereinbefore. Another group of suitable substances comprises those which, by binding to the nucleic acid, bring about an improvement in the transcription/expression thereof, by improving the accessibility of the nucleic acid for the expression machinery of the cell. An example of a substance of this kind is chromosomal non-histone protein HMG1, which has been found to possess the capacity to compact DNA and promotes expression in the cell.

With regard to the complexes, when determining the molar ratios of endosomolytic agent and/or internalizing factor/substance having an affinity for nucleic acid/nucleic acid(s), care should be taken that complexing of the nucleic acid(s) takes place, that the complex formed can be bound to the cell and internalized, and that, either by itself or with the aid of the endosomolytic agent is released from the endosomes.

The internalizing factor/binding factor/nucleic acid ratio depends particularly on the size of the polycation molecules and the number and distribution of the positively charged groups, criteria which are matched to the size and structure of the nucleic acid(s) to be transported. Preferably, the molar ratio of internalizing factor/substance having an affinity for a nucleic acid will range from about 10/1 to about 1/10.

After the construction and synthesis of the conjugates and determination of the optimum ratio of conjugate: DNA for effective transfection, the quantity of the conjugate proportion which can be replaced, if desired, by free substance having an affinity for nucleic acid can be determined by titration. If polycations are used both as the binding factor and also as a free substance having an affinity for nucleic acid, the polycations may be identical or different.

For the embodiment of the invention which employs viral conjugates a method suitable for determining the ratio of the components contained in the complexes may consist in first defining the gene construct which is to be introduced into the cells and, as described above, finding a virus or virus component which is suitable for the particular transfection. Then the virus or virus component is bound to a polycation and complexed with the gene construct. Starting from a defined quantity of viral conjugate, titrations may be carried out by treating the target cells with this (constant) quantity of conjugate and decreasing concentrations of DNA, or vice versa. In this way the optimum ratio of DNA:virus conjugate is determined. If an additional internalizing factor is used the procedure may be, for example, to determine the optimum ratio of virus conjugate to internalizing factor conjugate starting from a constant quantity of DNA by titration.

The complexes may be prepared by mixing together the components i) nucleic acid, ii) viral conjugate optionally iii) internalizing factor/binding factor conjugate, and optionally iv) non-covalently bound substance having an affinity to nucleic acid, all of which may be present in the form of dilute solutions. If polycations are used as a binding factor and at the same time as "free" polycations, it is generally advisable first of all to prepare a mixture of conjugates with "free" polycations and then combine this mixture with DNA. The optimum ratio of DNA to the conjugate(s) and polycations is determined by titration experiments, i.e. in a series of transfection experiments using a constant amount of DNA and increasing amounts of conjugate(s)/polycation mixture. The optimum ratio of conjugate(s): polycations in the mixture is obtained by routine experimentation or by comparing the optimum proportions of the mixtures used in the titration experiments.

The DNA complexes may be prepared at physiological salt concentrations. Another possibility is to use high salt concentrations (about 2M NaCl) and subsequent adjustment to physiological conditions by slow dilution or dialysis.

The most suitable sequence for mixing the components nucleic acid, conjugate(s), possibly non-covalently bound substance with an affinity to nucleic acid is determined by prior experimentation. In some cases, it may prove advisable first to complex the nucleic acid with the conjugate(s) and then to add the "free" substance with an affinity for nucleic acid, e.g. the polycation, e.g. in the case of conjugates of transferrin-ethidium dimer and polylysine.

In a preferred embodiment of the invention, the internalizing factor or the additional internalizing factor, respectively, is transferrin and the binding factor is a polycation. The term "transferrin" denotes both the natural transferrins and also those transferrin modifications which are bound by the receptor and transported into the cell.

The nucleic acid is taken up in the form of complexes in which internalizing factor-polycation conjugates are complexed with nucleic acid. When there is a content of a non-covalently bound substance with an affinity for nucleic acid, this is preferably a polycation. This second polycation is identical to or different from the polycation contained in the conjugate or in both conjugates.

In case of "combination complexes" the nucleic acid is internalized in the form of complexes in which internalization factor conjugates on the one hand and endosomolytic conjugates on the other hand are complexed with nucleic acid.

The conjugates of internalizing factor and polycation, which are used together with free virus or together with the viral conjugates in the combination complexes, may be prepared by a chemical method or, if the polycation is a polypeptide, by a recombinant method; for methods of preparation, reference is made to the disclosure of EP 388 758; the disclosure of which is fully incorporated by reference herein.

Preferably, within the scope of the present invention, conjugates are used in which the glycoprotein, e.g. transferrin, and the binding factor are connected to each other via one or more carbohydrate chains of the glycoprotein.

Unlike the conjugates prepared by conventional coupling methods, conjugates of this kind are free from modifications originating from the linker substances used. In the case of glycoproteins which have only one or a few carbohydrate groups suitable for coupling, e.g. transferrin, these conjugates also have the advantage that they are precisely defined in terms of their binding site for glycoproteins/binding factor.

A suitable method of preparing glycoprotein-polycation conjugates is disclosed in German Patent Application P 41 15 038.4; it was described recently by Wagner, E. et al. (1991) *Bioconjugate Chemistry* 2, 226–231.

The quantity of endosomolytic agent used and the concentration thereof depend on the particular transfection being undertaken. It is desirable to use the minimum quantity of virus or virus conjugate which is necessary to ensure the internalization of the virus (conjugate) and the nucleic acid complex and release from the endosomes. The quantity of virus (conjugate) is matched to the particular cell type and the infectivity of the virus for this type of cell must be taken into consideration above all. Another criterion is the particular conjugate of internalizing factor and binding factor, particularly with regard to the internalizing factor, for which the target cell has a specific number of receptors. Moreover, the quantity of virus (conjugate) will depend on the amount of DNA to be imported. Generally, a small mount of virus is sufficient for a stable transfection which requires only a small amount of DNA, whereas a transient transfection, which requires larger amounts of DNA, requires a larger quantity of virus. For a particular application, preliminary tests are carried out with the target cells intended for transfection, possibly with a mixed cell population, and the vector system envisaged for the transfection, in order to determine the optimum virus concentration by titration, while the DNA used is conveniently a gene construct which largely coincides with the one intended for concrete use, in terms of its size, and contains a reporter gene for easier measurement of efficiency of gene transfer. Within the scope of the present invention, the luciferase and β-galactosidase genes have been shown to be suitable reporter genes for such tests.

In general, it is preferred to apply nucleic acid complex and endosomolytic agent simultaneously, but they may also be applied one after the other. In case of separate applications, the sequence of application is not critical as long as the steps are carried out shortly after each other in order to guarantee that the components are in effective simultaneous contact.

In case of using free virus in a separate preparation, simultaneous administration of the preparation of free virus with the complexes may be guaranteed by having the virus preparation as part of the transfection medium which contains the nucleic acid complex.

In the case of simultaneous administration of free virus, the nucleic acid complexes and virus preparation are mixed together before being administered. In a preferred embodiment, the endosomolytic agent is a component of a combination complex. In order to increase gene expression, the compositions according to the invention may also be administered repeatedly.

It is known that lysosomatropic substances inhibit the activity of proteases and nucleases and may therefore inhibit the degradation of nucleic acids (Luthmann, H. and Magnusson, G. (1983) *Nucl. Acids Res.* 11, 1295–1308). These substances include chloroquine, monensin, nigericin and methylamine. It has been shown that monensin brings about an increase in the expression of reporter gene when a Moloney retrovirus is used.

The presence of chloroquine could be demonstrated to lead to expression of a reporter gene, imported by transferrin-mediated DNA transfer in virtually 100% of K562 cells. BNL.CL2 or HepG2 hepatocytes did not respond as well to chloroquine as did K562 cells but they could be transfected to a level of 5–10% when exploiting the endosomolytic properties of added replication defective or chemically inactivated free adenovirus.

In another aspect, the present invention relates to pharmaceutical compositions containing as active ingredient a complex of therapeutically active IRF-1 nucleic acid, preferably as part of a gene construct, endosomolytic agent (optionally conjugated) and optionally an internalizing factor conjugate, for administration to an animal, e.g. a human. Any inert pharmaceutically acceptable carrier may be used, such as saline, or phosphate-buffer saline, or any such carrier in which the DNA complexes have suitable solubility properties for use in the method of the present invention. Reference is made to Remington's Pharmaceutical Sciences, Mack Publishing Co., Easton, Pa. Osol (ed.) (1980) for methods of formulating pharmaceutical compositions.

The composition of the invention may occur as a lyophilisate or in a suitable buffer in deep-frozen state. It may also be provided as ready-to-use reagent in solution, preferably shipped cooled. Optionally, the components necessary for transfection, i.e. DNA, endosomolytic agent, optionally conjugated or ready for conjugation with a separate conjugation partner, DNA binding substance, optionally conjugated with an internalizing factor, optionally free polycation, may be present in a suitable buffer separate or partially separate as constituents of a transfection kit, which is also subject of the present invention. The transfection kit of the present invention comprises a carrier means having in close confinement therein one or more container means such as tubes, vials and the like, each of which contain the materials necessary to carry out the transfection of an animal cell in accordance with the present invention. In such a transfection kit, a first container means may contain one or more different DNAs. A second container means may contain one or more different internalizing factor conjugates that enable the use of the transfection kit as a modular system. Whether the constituents are supplied as a ready-to-use preparation or separately to be mixed immediately before use, depends, apart from the specific application, on the stability of the complexes, which can be determined routinely in stability tests. In a preferred embodiment, a transglutaminase coupled adenovirus-polylysine conjugate, which has proven to be stable at storage, is provided in one of the container means of a kit. In another preferred embodiment, biotinylated adenovirus and streptavidin-polylysine are provided in separate container means and are mixed before application. One of ordinary skill in the art can design numerous different transfection kits to take advantage of the flexibility of the invention.

For therapeutic use, the composition may be administered systemically, preferably by intravenous route, as part of a pharmaceutical composition. The target organs for this application may be, for example, the liver, spleen, lungs, bone marrow and tumors.

One example for local application is the lung tissue (use of the composition according to the invention as part of a pharmaceutical composition in fluid form for instillation or as an aerosol for inhalation). In addition, the pharmaceutical compositions of the invention may be administered by direct injection into the liver, the muscle tissue, into a tumor or by local administration in the gastro-intestinal tract. Another method of administration of the pharmaceutical composition is the application via the bile draining system. This method of application allows direct access to hepatocyte membranes at the bile canaliculi, avoiding interaction of the composition with blood constituents.

Recently, the feasibility of using myoblasts (immature muscle cells) to carry genes into the muscle fibres of mice has been shown. Thus, engineered myoblasts may be used to deliver IRF-1 gene products which either act in the blood or are transported by the blood. Both myoblast and myotube cultures, even primary ones, can be transfected with high efficiency. The most successful transfection media contained combination complexes of biotinylated adenovirus, transferrin-polylysine and streptavidin-polylysine. Besides the reporter genes luciferase and β-galactosidase, factor VIII was expressed in the muscle cells. Furthermore, the chicken adenovirus CELO was employed in combination complexes containing wheat germ agglutinin as an additional internalizing factor.

Therapeutic application may also be ex vivo, in which the treated cells, e.g. bone marrow cells, hepatocytes or myoblasts, are returned to the body (e.g., Ponder, J. P. et al., *Proc. Natl. Acad. Sci. USA* (1991) 88: 1217–1221; Dhawan, J. et al. (1991) *Science* 254: 1509–1512). Another ex vivo application of the present invention concerns so-called "IRF-1 cancer vaccines". The principle of this therapeutic approach is to isolate tumor cells from a patient, transfect the cells with IRF-1 DNA. The next step may involve inactivation of the cells, e.g. by irradiation, in such a way that they no longer replicate but still express the IRF-1 DNA. Then the genetically modified cells are applied to the patient from which they have been isolated, as a vaccine. In the environment of the vaccination site, the secreted IRF-1 protein activates other cells. These activated cells are able to exert their effect in other parts of the body and attack also non-treated tumor cells. Thus, the risk of tumor recurrency and of developing metastasis are reduced. A protocol suitable for the application of cancer vaccines for gene therapy was described by Rosenberg, St. A. et al. (1992) *Human Gene Therapy* 3: 75–90. Primary melanoma cells may be transfected with IRF-1 contained in combination complexes of polylysine-coupled adenovirus and transferrin-polylysine.

The present invention is described in further detail in the following non-limiting examples.

EXAMPLE 1

Figure 1B:
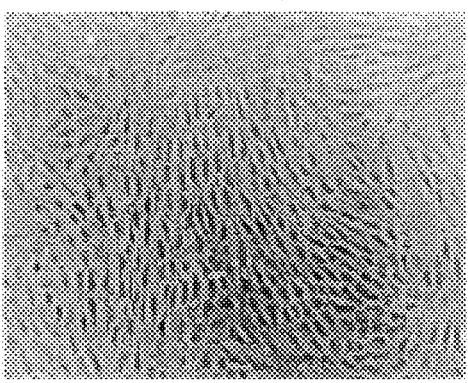
Figure 1C:
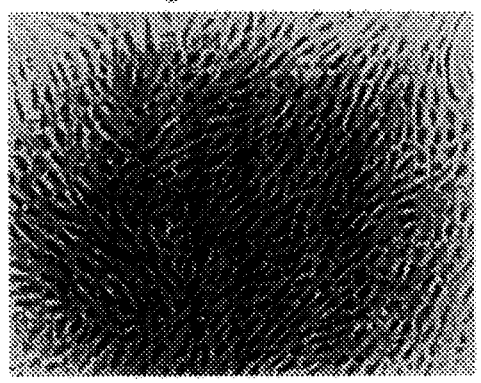
Figure 1D:
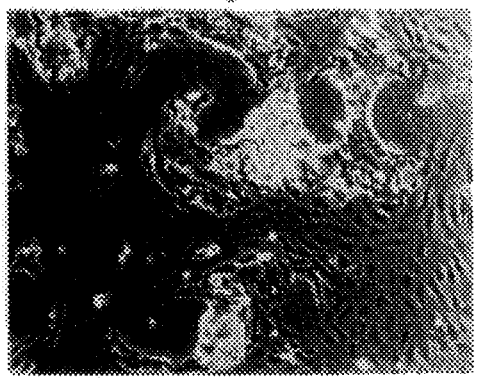
Figure 1E:
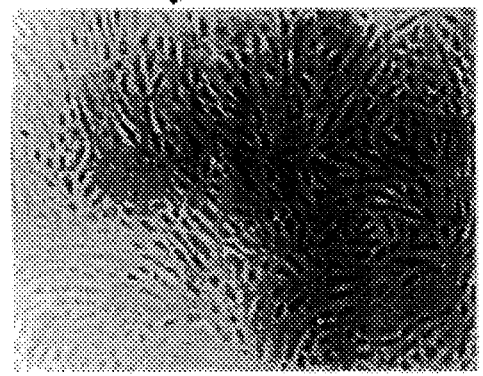
Figure 1F:
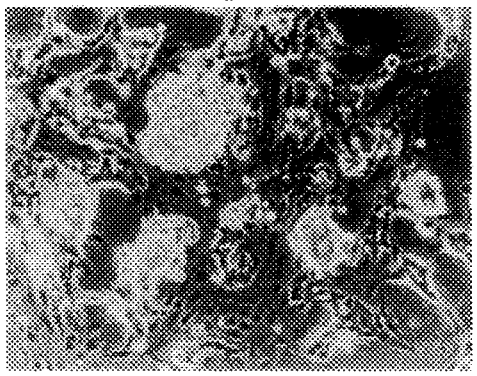
Figure 2A:
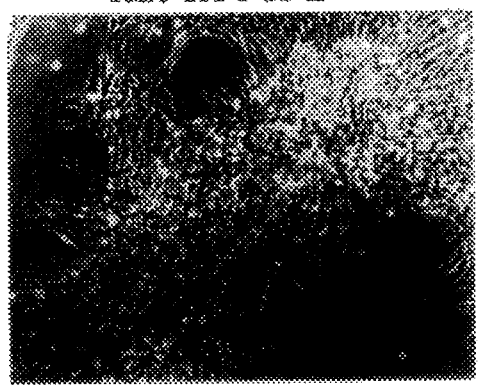
FIG. 2A–2F; Photographs of phenotypically reverted fosB-transformed Rat-1A cells following retroviral introduction of IRF-1. The cells were all photographed (magnification, ×100) in Dulbecco modified Eagle medium containing 10% fetal calf serum. Rat-1A-FosB (FIG. 2A); fosB transformed Rat-1A cells (Rat-1A (FIG. 2B) (FosB)), Rat-1A; untransformed Rat-1A cells, Fos B-IRF-1-1 (FIG. 2C) and Fos B-IRF1-2 (FIG. 2E); pGDIRF1 infected Rat-1A(FosB) cell clones, Fos B-C-1 (FIG. 2D) and Fos B-C2 (FIG. 2F); pGD infected Rat-1A(FosB) cell clones.
Figure 2B:
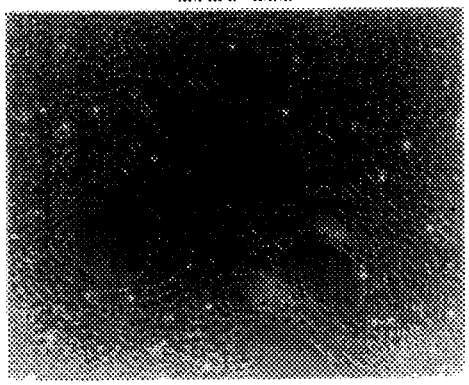
Figure 2C:
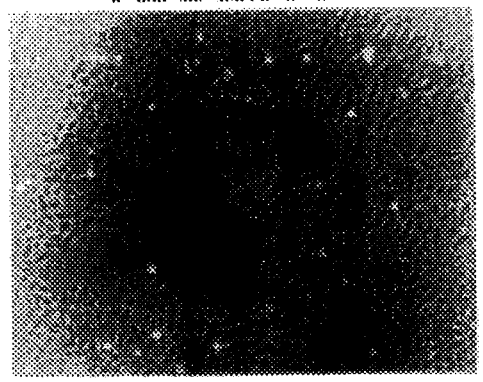
Figure 2D:
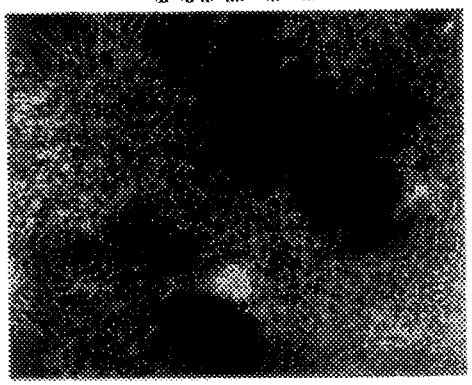
Figure 2E:
Figure 2F:
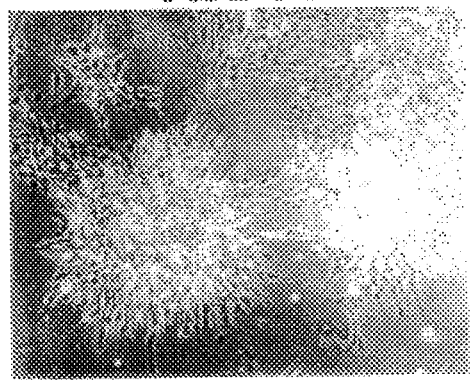

A retrovirus, pDGIRF1, which expresses murine IRF-1 upon infection, was constructed as previously described (Harada et al., *Science* 259: 971–974 (1993)). For this purpose, mouse IRF-1 cDNA (Miyamoto et al., *Cell* 54: 903–913 (1988)) was inserted into the pGD vector (Daley et al., *Science* 247: 824 (1990)). The DNA constructs were transfected into ψ2 cells (Mann et al., *Cell* 33: 153 (1983)), which subsequently released into the culture medium a high titer (~$10^6$ colony-forming units per milliliter) of virus, as assayed by the ability to confer neo resistance to NIH 3T3 cells. Expression of the IRF-1 protein was confirmed by gel-shift analysis. The c-myc-transformed 3Y1 cell or fosB-transformed Rat-1A cell, termed RmycY1 and Rat-1A (FosB), respectively, both show anchorage-independent growth and enhanced tumorigenicity in rat or nude mice (Shiroki et al., *Mol. Cell. Biol.* 6: 4379–4386 (1986); Nakabeppu et al., *Mol. Cell. Biol.* 13: 4157–4166 (1993)). $5\times10^5$ of each cells were infected by the pDGERF-1 virus at the multiplicity of infection (m.o.i.) of 10, using exactly the method employed by Harada et al., and subsequently limiting diluted to obtain single clones. Morphologic investigations and tumorigenicity tests (nude mice model) were performed by standard procedures. After 1 or 2 weeks, these cell clones have lost the transformed phenotype. In fact, these vitally infected cells have changed the morphology which is indistinguishable from the original Rat 1 cells (FIGS. 1, 2), and lost their tumorigenic potential in nude mice (Table 1).

In contrast, no such change was observed by infecting similarly the control retrovirus pGD (FIGS. 1, 2). Thus, these observations clearly indicate the broad function of IRF-1 as tumor suppressor in cells transformed by at least two different oncogenes. The levels of the oncogene messenger RNAs expressed in these reverted cells remained essentially the same as the original, transformed cells. Therefore, the observed phenotypic reversion of the cells as the result of IRF-1 gene expression is not due to the inhibition of the promoters used for the oncogene expression.

TABLE 1

Growth properties of RmycY1 and Rat-1A(FosB) cells overexpressing IRF-1

| Cells | Growth efficiency (%) in methylcellulose gel* | Tumorigenicity† Tumors per injection | Latency (weeks) |
|---|---|---|---|
| RmycY1 | 28, 26 | 6/6 | 3 to 4 |
| 3Y1 | 0, 0 | 0/6 | |
| myc-IRF1-1 | <1, <1 | 0/2 | |
| myc-IRF1-2 | <1, <1 | 0/2 | |
| myc-IRF1-3 | <1, <1 | 0/2 | |
| myc-IRF1-4 | <1, <1 | 0/2 | |
| myc-C-1 | 32, 34 | 2/2 | 3 to 4 |
| myc-C-2 | 30, 28 | 2/2 | 3 to 4 |
| Rat-1A(FosB) | 24, 28 | 4/4 | 2 to 4 |
| Rat-1A | 0, 0 | 0/4 | |
| Fos B-IRF1-1 | <1, <1 | 0/2 | |
| Fos B-IRF1-2 | <1, <1 | 0/2 | |
| Fos B-IRF1-3 | <1, <1 | 0/2 | |
| Fos B-IRF1-4 | <1, <1 | 0/2 | |
| Fos B-C-1 | 26, 25 | 2/2 | 3 to 4 |
| Fos B-C-2 | 18, 22 | 2/2 | 3 to 4 |

*Cells ($5 \times 10^5$) were mixed with 1.3% methylcellulose gel dissolved in culture medium and layered onto an agarose bed composed of 0.53% agarose and culture medium (Harada et al., Science 259:971-974 (1993)).
†Four- to six-week-old nude mice (BALB/c nu/nu) were injected subcutaneously on both franks with $2 \times 10^6$ cells and tumors were scored as described by Harada et al.

All patent applications and publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A method of inhibiting the growth of tumor cells expressing c-myc or fosB comprising:
   (a) introducing to said cells in vitro a DNA sequence encoding interferon regulatory factor 1 (IRF-1), and
   (b) expressing said DNA sequence such that the growth of said cells is inhibited.

2. The method according to claim 1, wherein said cells lack tumor suppressor gene expression.

3. The method according to claim 1, wherein said DNA sequence is comprises in a viral vector.

4. The method according to claim 3, wherein said viral vector is a retrovirus.

5. The method according to claim 4, wherein said retrovirus is pDGIRF-1.

* * * * *